US012629117B2

(12) United States Patent
Tran et al.

(10) Patent No.: US 12,629,117 B2
(45) Date of Patent: May 19, 2026

(54) MOBILE X-RAY DEVICE DETECTOR GRID HANDLE

(71) Applicant: GE Precision Healthcare LLC, Waukesha, WI (US)

(72) Inventors: Richie Tran, Milwaukee, WI (US); Andrew G. Van Hulle, New Berlin, WI (US)

(73) Assignee: GE Precision Healthcare LLC, Waukesha, WI (US)

( * ) Notice: Subject to any disclaimer, the term of this patent is extended or adjusted under 35 U.S.C. 154(b) by 241 days.

(21) Appl. No.: 18/641,961

(22) Filed: Apr. 22, 2024

(65) Prior Publication Data

US 2025/0325241 A1      Oct. 23, 2025

(51) Int. Cl.
  *A61B 6/42*          (2024.01)
  *A61B 6/00*          (2024.01)

(52) U.S. Cl.
  CPC .......... *A61B 6/4291* (2013.01); *A61B 6/4405* (2013.01)

(58) Field of Classification Search
  CPC .... A61B 6/4291; A61B 6/4405; A61B 6/4283
  See application file for complete search history.

(56) References Cited

U.S. PATENT DOCUMENTS 7,104,686 B2 *  9/2006  Watanabe ............. G01T 1/2928
                                              378/189
7,852,985 B2 * 12/2010  Liu ......................... G01T 1/175
                                              250/370.08

7,896,544 B2     3/2011  Nagashima et al.
D683,459 S  *   5/2013  Haltof ........................... D24/161
9,839,406 B2   12/2017  Urbon et al.
                (Continued)

FOREIGN PATENT DOCUMENTS

CN          118680586 A  *  9/2024  ............... A61B 6/42
DE      102004061506 A1 *  6/2006  ........... A61B 6/4283
                (Continued)

OTHER PUBLICATIONS

14×17In Tri-Handle Handle Mobile DR Panel Holder, Reinal Imaging, https://www.reinaimaging.com/product/14x17in-tri-handle-handle-mobile-dr-panel-holder/.

*Primary Examiner* — Edwin C Gunberg
*Assistant Examiner* — Richard O Toohey
(74) *Attorney, Agent, or Firm* — Boyle Fredrickson, S.C.

(57)          ABSTRACT

A grid handle for a detector utilized with a mobile x-ray device includes an encasement for releasably receiving and retaining the detector therein. The encasement has a body including an interior adapted to receive the detector therein, a handgrip extending along a top edge of the body and an auto-locking mechanism disposed on the body and operable to secure the detector within the interior of the body. The auto-locking mechanism includes a latch moveably mounted to the body, a first biasing member engaged between the latch and the body, a lock moveably mounted to the latch and the body, and a second biasing member engaged between the lock and the body. The auto-locking mechanism does not require addition components for assembly on the encasement, and the encasement can include a grip enhancement structure disposed on the handgrip and a securing tab opposite the auto-locking mechanism to define a connector space.

20 Claims, 11 Drawing Sheets

(56)  References Cited

U.S. PATENT DOCUMENTS

| | | | | |
|---|---|---|---|---|
| D864,394 | S | 10/2019 | Kumar et al. | |
| 2009/0202038 | A1* | 8/2009 | Wu ...................... | A61B 6/4429 |
| | | | | 378/198 |
| 2009/0202044 | A1* | 8/2009 | Wu ...................... | A61B 6/4233 |
| | | | | 378/189 |
| 2011/0133085 | A1* | 6/2011 | Konkle ................. | G03B 42/04 |
| | | | | 156/247 |
| 2013/0077760 | A1 | 3/2013 | Tagawa | |
| 2025/0281132 | A1* | 9/2025 | Heckel ................ | A61B 6/4405 |

FOREIGN PATENT DOCUMENTS

| | | | | | |
|---|---|---|---|---|---|
| EP | 2380495 | A1 * | 10/2011 | ............ | G03B 42/02 |
| JP | 2005258370 | A | 9/2005 | | |
| JP | 5597291 | B2 | 10/2014 | | |
| JP | 2015083126 | A * | 4/2015 | | |
| WO | WO-2011064968 | A1 * | 6/2011 | ........... | G03B 42/047 |

* cited by examiner

MOBILE X-RAY DEVICE DETECTOR GRID HANDLE

FIELD OF THE DISCLOSURE

The present disclosure is related to x-ray imaging devices, and more particularly to grid handles used to hold and position detectors for mobile x-ray imaging devices.

BACKGROUND OF THE DISCLOSURE

Digital imaging technologies including medical imaging technologies such as x-ray imaging allow for non-invasive acquisition of images of internal structures or features of a subject, such as a patient. Digital imaging systems produce digital data which can be reconstructed into radiographic images. In digital x-ray imaging systems, radiation from a source is directed toward the subject. A portion of the radiation passes through the subject and impacts a detector. The detector includes an array of discrete picture elements or detector pixels and generates output signals based upon the quantity or intensity of the radiation impacting each pixel region. The output signals are subsequently processed to generate an image that may be displayed for review. These images are used to identify and/or examine the internal structures and organs within a patient's body.

In order to facilitate obtaining x-ray images in a variety of locations and/or situation a number of mobile x-ray devices have been developed. These mobile x-ray devices have particular applicability in situations where the patient cannot or is not readily moveable, such that it is required to move the imaging device to the patient. The construction of the mobile x-ray device includes a mobile chassis that supports the entire x-ray assembly and a telescopic column that is mounted on the chassis. The telescopic column includes a fixed portion jointed to the chassis, and one or more telescopic portions that are movably mounted to the fixed portion. The telescopic portion also includes a telescopic arm opposite the fixed portion that can move along the telescopic portion and that supports an x-ray emitter or source opposite the telescopic portion.

In operation the mobile chassis can be moved into a location adjacent the patient or other object to be imaged. Then, employing the mechanisms disposed within the fixed portion and the telescopic portion, the telescopic arm and x-ray emitter can be moved to the desired position in order to obtain the x-ray images of the patient. The mechanisms allow the telescopic portion and telescopic arm to be moved and counterbalanced by the remainder of the mobile x-ray device, thereby enabling the x-ray emitter to be properly and stably positioned to obtain the desired x-ray images.

The mobile x-ray device additionally includes one or more detectors associated with the mobile x-ray device. These detectors are capable of receiving the x-rays from the x-ray emitter that are directed through the patient and transmitting the information to the processing unit within the mobile chassis for generation of an x-ray image. The generated x-ray image can be presented on a display located on the mobile chassis in order to determine a proper course of treatment for the patient.

The detectors used in the imaging procedures performed with the mobile x-ray imaging device can be stored within a bin disposed on the chassis opposite the telescopic portion. The bin has dimensions that approximate the dimensions of the detectors, such that the detectors can be securely retained within the bin during movement of the mobile x-ray device. The bin is disposed adjacent a bottom edge of the chassis to maintain the bin and detectors therein in an easy to access location that does not interfere with the operation and/or movement of the mobile x-ray device by the operator.

The detectors used with the mobile x-ray device can be operably connected by a wire or tether, or can be wirelessly connected to the processing device within the mobile chassis in order to transmit information and image data between the detector and the mobile chassis.

To facilitate the handling of the detectors to place them in the desired position relative to the patient and to obtain the desired image data to generate the x-ray image, the detector being used can be positioned within a grid handle. The grid handle functions in part to provide a protective and more easily handled frame for the detector. In particular, the grid handle includes a housing that corresponds in size to the shape and perimeter of the detector to position the detector therein. The housing includes a handgrip at one end that can be manually engaged by the user or technician to move the grid handle and the detector with one hand while manipulating the patient with the other hand to position the detector where necessary to obtain the desired image data.

To assist in obtaining the image data on the detector, the housing includes an anti-scatter grid. The grid is fixedly retained within the housing opposite the detector to align the detector with the grid when the detector is engaged within the housing. The housing can be oriented by the technician to place the grid between the radiation source and the detector to enable the grid to provide the anti-scatter function to the x-rays reaching the detector and enhance the quality of the image data.

To retain the detector within the housing of the grid handle, the grid handle can include a lock disposed on the housing. To retain the detector within the housing, after positioning the detector within the housing, the lock can be engaged with the detector. When it is desired to remove the detector from the grid handle, the lock can be disengaged from the detector allowing the detector to be removed from within the housing.

However, the locking devices utilized in prior art grid handles require the technician to actively engage the locking device with the detector to secure the detector within the housing. As such, on certain occasions the locking device is not engaged, or not fully engaged, such that the detector is not adequately secured within the housing and can become inadvertently displaced from within the housing during use, potentially damaging the detector.

Further, as the detectors are often wirelessly connected to the mobile x-ray device, the detectors include their own internal power supply for operation of the detector. To charge this power supply between uses, the detector is engaged with a charging port disposed within the storage bin located at the rear of the mobile x-ray device. However, with prior art grid handles, the housing within which the detector s disposed covers the charging connector on the detector. Thus, the prior art grid handles are required to be disengaged from the detector to enable the detector to be positioned within the bin and engaged with the charging port to recharge the internal power supply for the detector.

Also, in order to prevent the grid handle from interfering with the x-rays emitted by the x-ray source reaching the detector, other than through the desired operation of the anti-scatter grid located within the grid handle, the grid handle is formed from a x-ray transparent material. As detectors can be quite heavy, it is desirable to make the grid handle as lightweight as possible to minimize the weight that must be manipulated by the technician when positioning the detector. Thus, the grid handle is most often formed of a lightweight plastic material, such as a polyethylene, that is x-ray transparent and lightweight, while also providing sufficient durability to the grid handle.

Unfortunately, the polyethylene material also has an inherent low coefficient of friction. This attribute of the material imparts a slippery feel to the material and makes it difficult to securely engage the handgrip. As a result, the hand of the technician often slides along the handgrip when moving the grid handle and detector, greatly increasing the grip strength needed to securely grab the handgrip and avoid slippage of the handgrip during placement of the grip handle and detector.

As a result, it is desirable to develop a grid handle for a mobile x-ray device detector that has an improved construction that enables effective and reliable engagement of detectors therein with enhanced ease of manipulation of the grid handle in positioning the grid handle and detector that avoids the shortcomings of the prior art.

SUMMARY OF THE DISCLOSURE

According to one aspect of an exemplary embodiment of the disclosure, a grid handle for a detector utilized with a mobile x-ray device includes an encasement for releasably receiving and retaining the detector therein, the encasement having a body including an interior adapted to receive the detector therein, a handgrip extending along a top edge of the body, and an auto-locking mechanism disposed on the body and operable to secure the detector within the interior of the body; the auto-locking mechanism including a latch moveably mounted to the body, a first biasing member engaged between the latch and the body, a lock moveably mounted to the latch, and a second biasing member engaged between the lock and the body.

According to another exemplary embodiment of the disclosure, a method for positioning a detector within a grid handle includes the steps of providing a grid handle having an encasement for releasably receiving and retaining the detector therein, the encasement including a body including an interior adapted to receive the detector therein, a handgrip extending along a top edge of the body, and an auto-locking mechanism disposed on the body and operable to secure the detector within the interior of the body; the auto-locking mechanism having a latch moveably mounted to the body, a first biasing member engaged between the latch and the body, a lock moveably mounted to the latch, and a second biasing member engaged between the lock and the body, disengaging the lock on the latch, moving the latch from a closed position to an open position, placing the detector within the interior of the body, and releasing the latch to move into the closed position over at least a portion of the detector.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Figure 1:
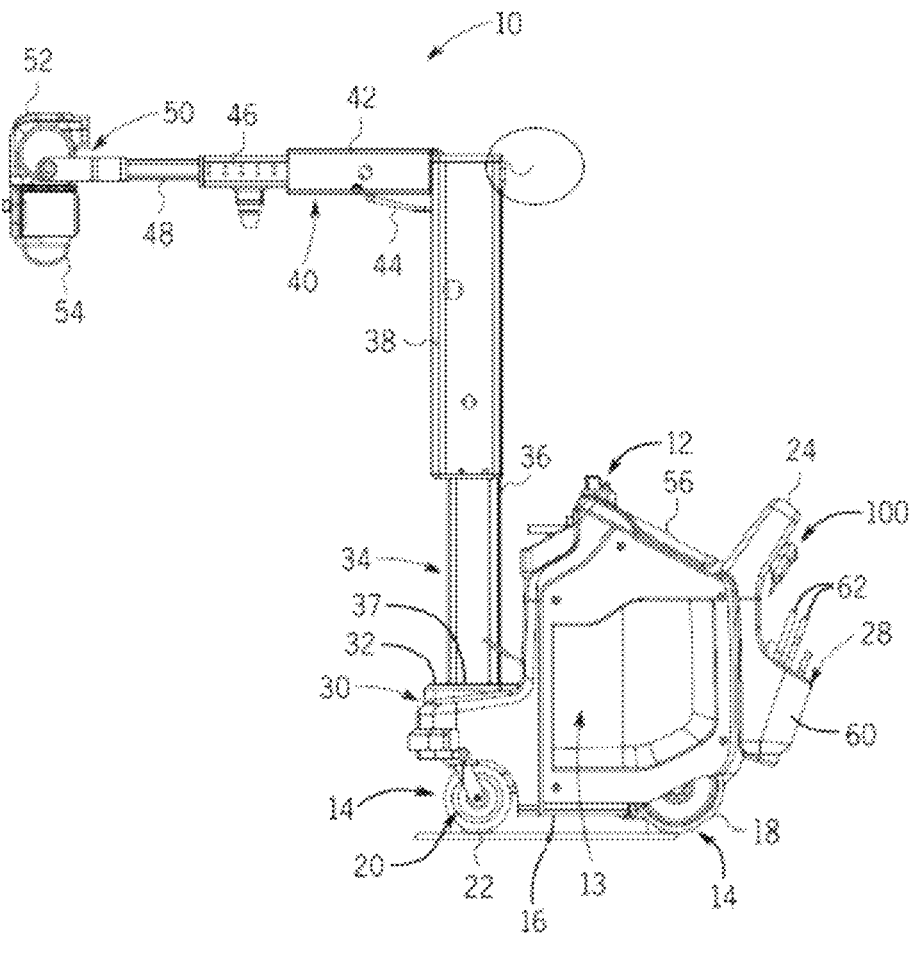
FIG. 1 is a side elevation view of a mobile x-ray device, according to an exemplary embodiment of the disclosure.
Figure 2:
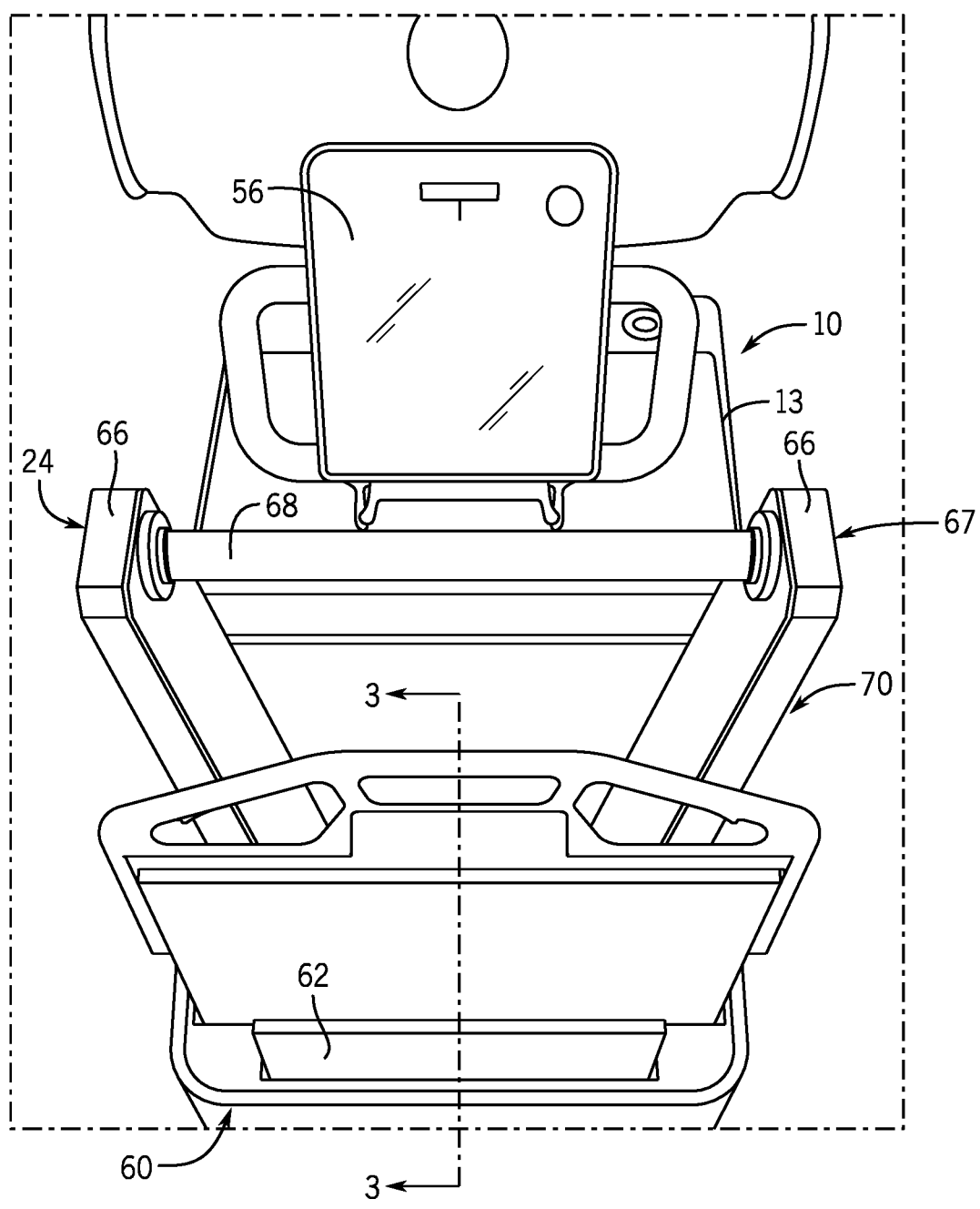
FIG. 2 is a rear elevation view of the mobile x-ray device of FIG. 1 with a detector retained in a grid handle in a storage bin of the mobile x-ray device, according to an exemplary embodiment of the disclosure.
Figure 3:
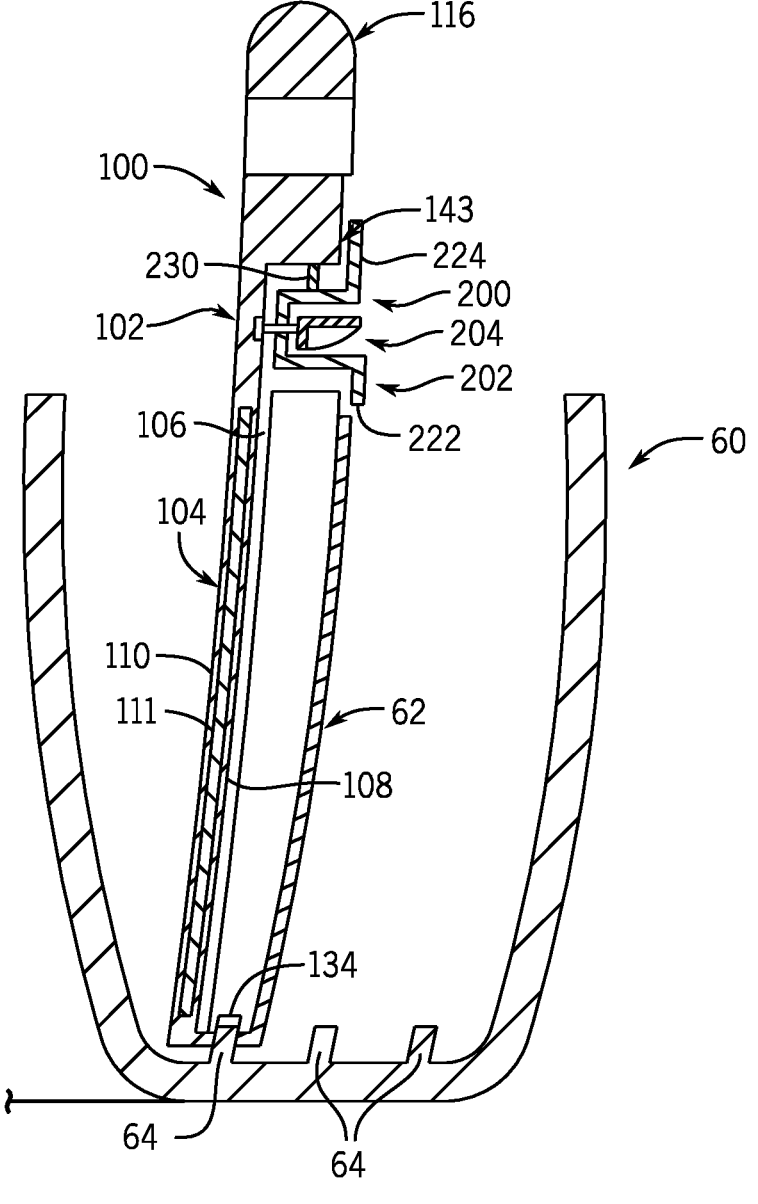
FIG. 3 is a cross-sectional view along line 3-3 of the bin of the mobile x-ray device, detector, and grid handle of FIG. 2, according to an exemplary embodiment of the disclosure.
Figures 4, 5, 6:
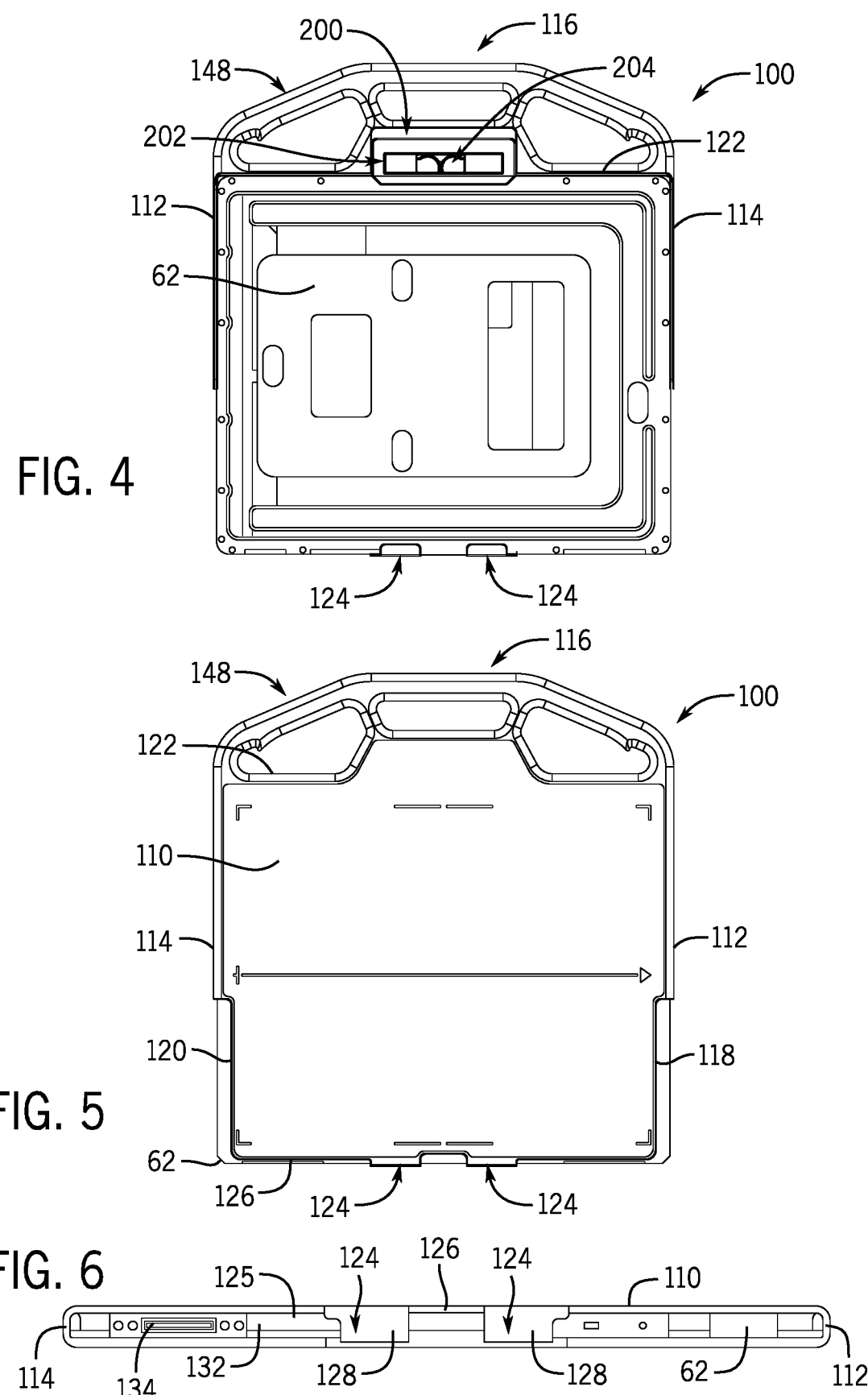
FIG. 4 is a front isometric view of a grid handle including a detector disposed thereon, according to an exemplary embodiment of the disclosure.
FIG. 5 is a rear isometric view of the grid handle of FIG. 4 including a detector disposed thereon, according to an exemplary embodiment of the disclosure.
FIG. 6 is a bottom elevational view of the grid handle of FIG. 4 including a detector disposed thereon, according to an exemplary embodiment of the disclosure.
Figures 7, 8:
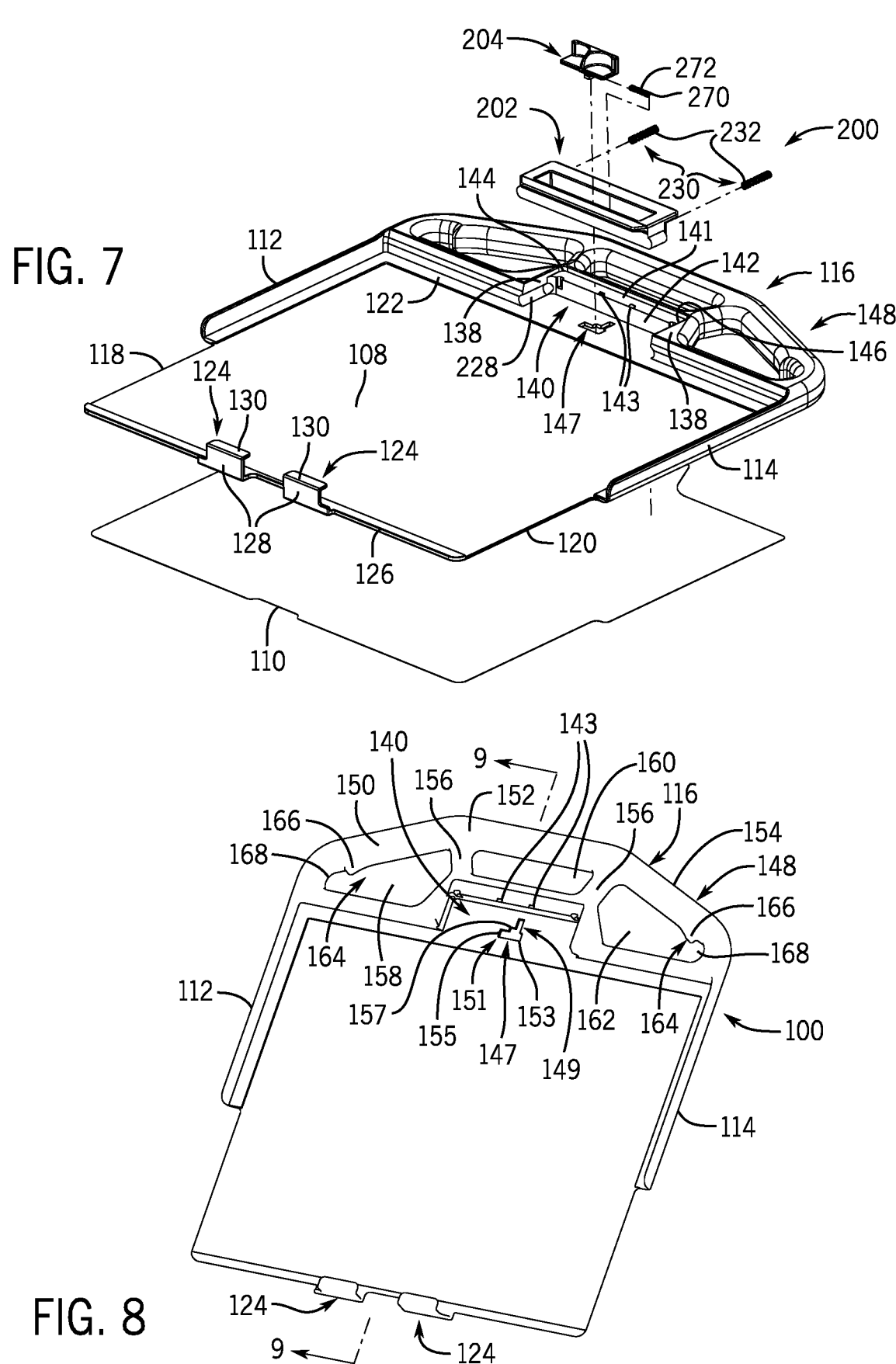
FIG. 7 is an exploded isometric view of the grid handle of FIG. 4.
FIG. 8 is an isometric view of an encasement of the grid handle of FIG. 4, according to an exemplary embodiment of the disclosure.
Figure 9:
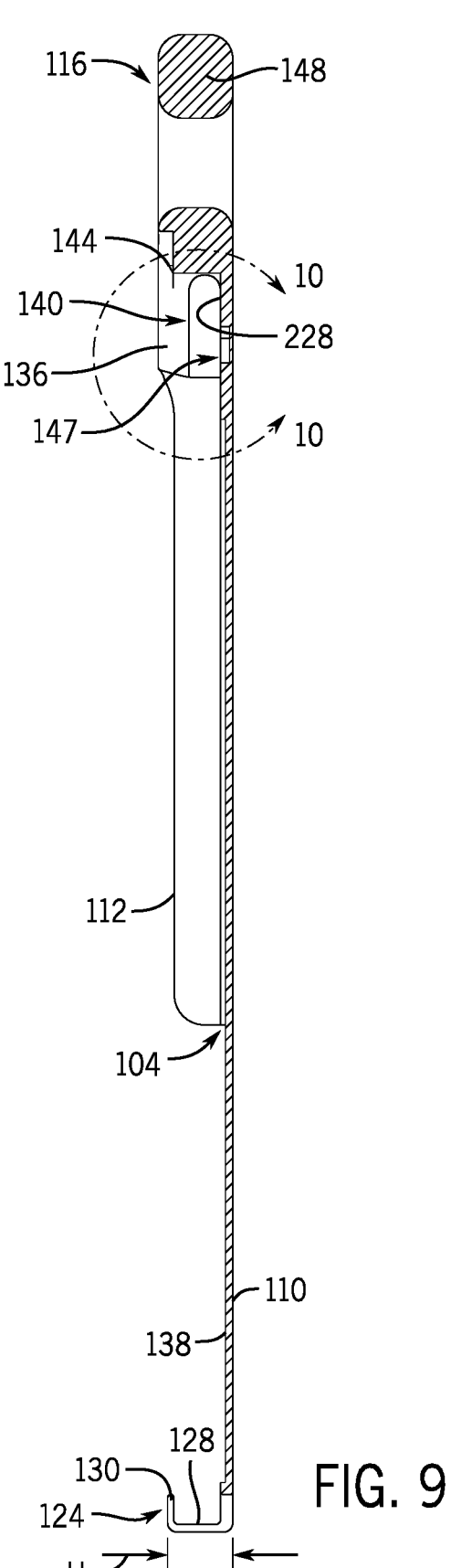
FIG. 9 is a cross-sectional view along line 9-9 of FIG. 8.
Figure 10:
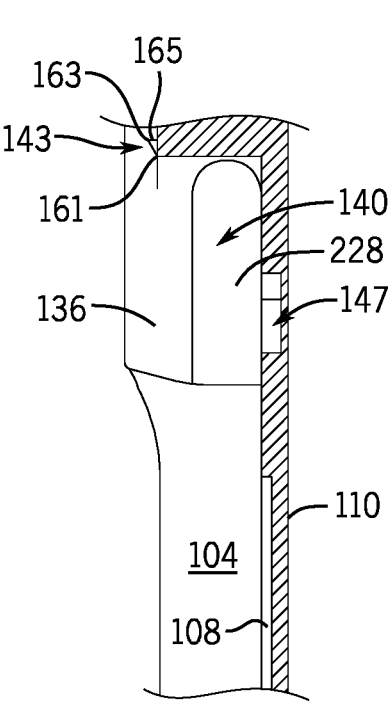
FIG. 10 is a sectional view along line 10-10 of FIG. 9.
Figure 11:
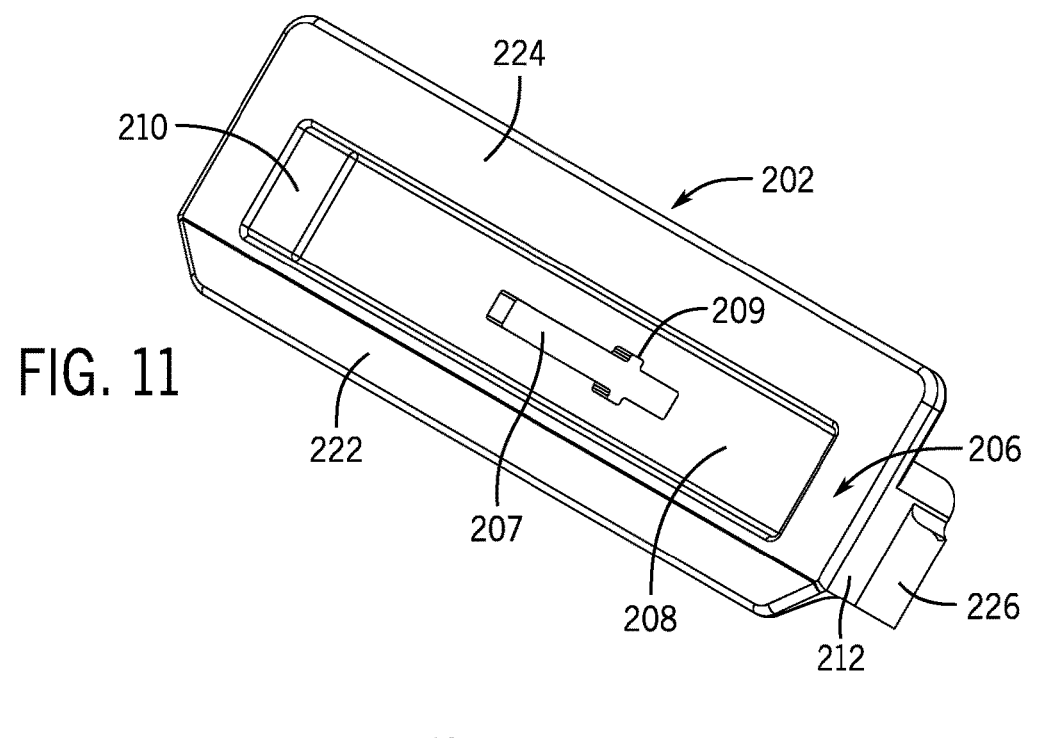
FIG. 11 is an isometric view of an auto-locking latch disposed on the grid handle of FIG. 4, according to an exemplary embodiment of the disclosure.
Figure 12:
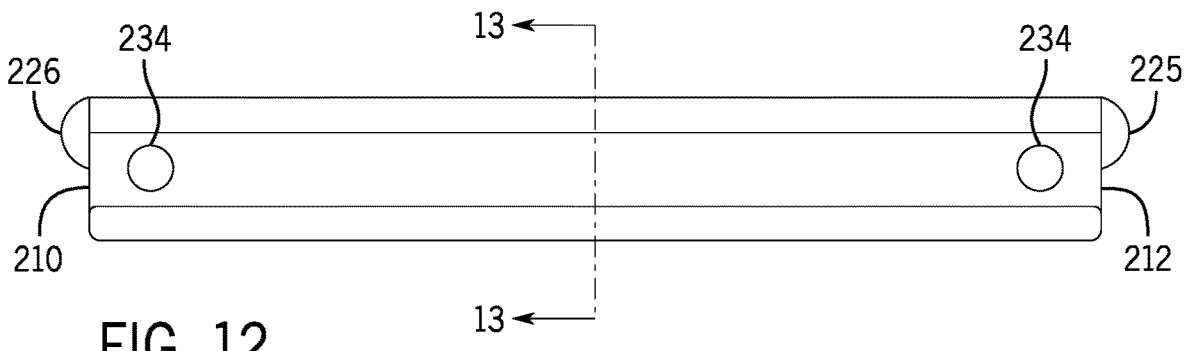
FIG. 12 is a rear elevational view of the auto-locking latch of FIG. 11.
Figure 13:
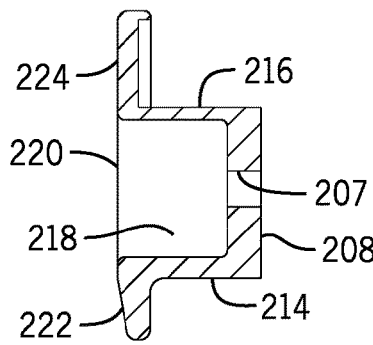
FIG. 13 is a cross-sectional view along line 13-13 of FIG. 12.

In FIGS. 1-3, an exemplary embodiment is illustrated of a mobile x-ray device 10 constructed according to the disclosure. The mobile x-ray device 10 includes a chassis 12 that defines a body 13 including a number of wheels 14 attached to a lower surface 16 of the body 13 in order to allow the mobile x-ray device 10 to be moved over a surface by a technologist. The wheels 14 can include a pair of large support wheels 18 located on an axle (not shown) directly secured to the chassis 12, and one or more directional wheels 20 affixed to the chassis 12 in a pivotal manner, such as casters 22, to facilitate the movement of the chassis 12 in a desired direction. The chassis 12 can additionally include a drive handle 24 extending outwardly from the chassis 12 and graspable by a technician in order to manually direct the movement of the chassis 12 where desired. In an alternative embodiment or as an addition to the above embodiment, the chassis 12 may include a suitable motor (not shown) that is operably connected to the wheels 14, such as to the support wheels 18, in order to provide motorized movement capability to the chassis 12.

The body 13 of the chassis 12 defines a rear end 28 and a front end 30. Within the rear end 28 the body 13 encloses a number of operative computers, processing units and/or systems (not shown) as are well-known for use in the mobile x-ray device 10 such as the processing units and/or operative systems for the obtaining and processing of x-ray data to provide x-ray images using the mobile x-ray device 10. The front end 30 defines a platform 32 that supports that supports a telescopic column 34 that can be moved as desired to position an x-ray emitter 52 attached to the column 34 where necessary to obtain the x-ray images.

The telescopic column 34 includes a lower fixed portion 36 disposed on the platform 32, where the fixed portion 36 is attached to the platform 32 by a suitable rotation mechanism (not shown) by a rotational collar 37 secured to the fixed portion 36 and rotatable with respect to the platform 32, that enables the fixed portion 36 to rotate with regard to the platform 32 along a vertical axis extending upwardly from the platform 32 through the fixed portion 36.

The column 34 additionally includes an upper telescopic portion 38 that is moveably attached to the fixed portion 36, such by a number of bearings (not shown) attached to the telescopic portion 38 and moveably disposed within guides (not shown) formed in the fixed portion 36. The upper telescopic portion 38 can move vertically with respect to the fixed portion 36.

Opposite the lower fixed portion 36, the upper telescopic portion 38 supports a telescoping arm 40. The telescoping arm 40 is movable vertically with regard to the telescopic portion 38. In an exemplary embodiment, the arm 40 is engaged with the telescopic portion 38 by a number of bearings (not shown) attached to the telescoping arm 40 and moveably disposed within guides (not shown) formed in the telescopic portion 38.

The telescoping arm 40 includes a fixed section 42 secured to a carriage 44 that is movably disposed on the telescopic portion 38, such as by bearings (not shown) formed on the carriage 44 and engaged in guides (not shown) in the telescopic portion 38, to provide the vertical movement of the telescoping arm 40 relative to the telescopic portion 38 of the column 34. A number of independently moveable sections 46,48 are secured to the fixed section 44 and can be selectively moved in a horizontal direction with regard to the fixed section 44 and one another to extend and retract the telescoping arm 40 relative to the telescopic portion 38.

Opposite the telescoping portion 38 the telescoping arm 40 supports a head assembly 50 on the outermost moveable section 48. In the illustrated exemplary embodiment of FIG. 1, the head assembly 50 is for obtaining x-ray images. The head assembly 50 in the illustrated embodiment includes an x-ray source or emitter 52 and a collimator 54, and is secured to the moveable section 48 in any suitable manner that enables the head assembly 50 to pivot and/or rotate relative to the moveable section 48 in order to position the emitter 52 where necessary to obtain the desired x-ray images.

The various components of the telescopic column 32, i.e., the fixed portion 36 and the telescopic portion 38, and the telescoping arm 40, i.e., the fixed section 44 and the moveable sections 46,48, are each formed of a material that is sufficiently rigid to support the various components of the x-ray device 10 that are attached thereto, while also be able to be formed with a hollow interior to enable various wiring and other operational connections between body 13 and the emitter 52, such as through an aperture (not shown) in the platform 32 beneath the column 34, for the operation of the x-ray device 10 to be made completely within the interior of the x-ray device 10.

Looking now at FIGS. 1-2, the mobile x-ray device 10 additionally includes a user console/display 56 on the body 13 in front of the drive handle 24 for the display of x-ray images obtained by the x-ray device 10 and/or for the operational control of the emitter 52 to obtain the x-ray images. In other embodiments, the console 56 can be disposed on an arm (not shown) that can be grasped by the user/technician to control the movement of the x-ray device 10. The user console 56 can be rotated with regard to the arm between 0° and 90° on the horizontal axis between use and storage positions, and additionally can rotate between −180° and +180° on the vertical axis. Further, the drive handle 24 includes a pair of arms 66 that extend outwardly from the chassis 12 on each side of the body 13. Opposite the body 13, the arms 66 include a bar 68 extending therebetween. The angle of the arms 66 in relation to the body 13 positions the bar 68 at an ergonomically acceptable location where an individual can easily grasp the bar 68 to readily control the movement of the mobile x-ray device 10 while also providing sufficient room for the individual to walk normally behind the mobile x-ray device 10 without inadvertently contacting, e.g., kicking, the mobile x-ray device 10.

The rear end 28 additionally includes a storage bin 60 extending outward from the rear end 28 below the drive handle 24. The storage bin 60 is configured to retain a number of detectors 62 therein, each of the detectors 62 operably connected, e.g. via a wired connection (not shown) or wirelessly, to the operative systems disposed within the body 13 in order to able to be utilized with the x-ray device 10 in an imaging procedure, e.g., to transmit image data from the detector 62 to the x-rays device 10. The bin 60 includes spaces therein for detectors 62 of differing sizes in order to hold the detectors 62 in a manner that prevents damage to the detectors 62 from outside contact and contact with one another.

Additionally, as best shown in FIG. 3, where the detectors 62 are wirelessly connected to the mobile x-ray device 10, the detectors 62 include an internal power supply (not shown) for the operation of the detector 62. The internal power supply can be recharged by the x-ray device 10 via charging ports (64) disposed within the bin 60 that are connected to a power source (not shown) for the mobile x-ray device 10. The charging ports (64) are oriented within the bin 60 in a position where the ports 64 can be engaged with connectors 66 disposed on the detectors 62 to enable charging of the internal power supply of the detector 62 when the detectors 62 are placed within the bin 60.

Looking now at the illustrated exemplary embodiment of FIGS. 4-14, in order to facilitate the movement of a detector 62 from within the bin 60 and into a desired location with regard to a patient (not shown) for the performance of an imaging procedure using the mobile x-ray device 10, the detector 62 is disposed within a grid handle 100. The grid handle 100 includes an encasement 102 that defines an interior 104 within which the detector 62 is releasably disposed.

With regard specifically to FIGS. 3-9, the encasement 102 includes a body 106 containing the interior 104 and formed of an x-ray transparent material, such as a plastic material including a polyethylene, e.g., a high density polyethylene, that has a generally flat upper surface 108 against which the detector 62 is positioned, and a generally flat lower surface 110. Within the body 106 between the upper surface 108 and the lower surface 110 is disposed an anti-scatter grid 111. When the detector 62 disposed within the grid handle 100 is in use, the grid handle 100 is positioned with the lower surface 110 between the detector 62 and the x-ray emitter 52 such that the anti-scatter grid 111 the enable the anti-scatter grid to provide the anti-scatter function to the x-rays reaching the detector and enhance the quality of the image data produced by the detector 62.

The encasement 102 further includes a pair of side panels 112,114 extending outwardly from opposed side edges 118, 120 of the upper surface 108. The side panels 112,114 are joined by a handgrip 116 extending outwardly from a top edge 122 of the upper surface 108 and between the side panels 112,114. Each of the side panels 112,114 can be formed to extend along the associated side edge 118,120 of the upper surface 108, and in the illustrated exemplary embodiment along only a portion of the associated edge 118,120 to expose a section of the associated side edge 118,120 opposite the handgrip 116.

Opposite the handgrip 116, which can be formed as part of the body 106, one or more securing tabs 124 extend outwardly from a bottom edge 126 the upper surface 108 in the same direction as the side panels 112,114 and the handgrip 116 in order to define the interior 104 of the encasement 102. In the illustrated exemplary embodiment, a pair of securing tabs 124 are spaced from one another on the bottom edge 126 with each securing tab 124 including an outwardly extending section 128 and an inwardly extending section 130. The outwardly extending section 128 has a height H (FIG. 9) above the upper surface 108 similar to that for the side panels 112,114 and the handgrip 116 to define the interior 104 to accommodate the corresponding dimension of the detector 62 to be positioned and retained within the interior 104 of the encasement 102. Further, the inwardly extending section 130 has a length sufficient to overlap a portion of the detector 62 positioned within the interior 104 of the encasement 102. Thus, the overlap provided by the inwardly extending section 130 of the securing tabs 124 operates to retain the detector 62 within the interior 104.

The positioning of the one or more securing tabs 124 along the bottom edge 126 of the upper surface 108 enables the encasement 102 to expose one or more portions of a bottom end 132 of the detector 62 when the detector 62 is positioned within the interior 104 of the encasement 102. In one exemplary embodiment, the location(s) of the securing tabs 124 can be selected, at least in part, to form a connector space 125 therebetween to expose a charging connector 134 located on the bottom end 132 of the detector 62. The exposure of the charging connector 134 within the connector space 125 defined by the securing tabs 124 enables the charging connector 134 to be readily engaged with a charging port 64 located within the bin 60 when the detector 62 held within the grid handle 100 is inserted into the bin 60. Thus avoids the necessity for removal of the detector 62 from the grid handle 100 prior to placement within the bin 60 for proper charging of the detector 62, as in prior art grid handles.

Referring now to FIGS. 4-5 and 7-10, in addition to extending outwardly from the top edge 122 in the same direction as the side panels 112,114 and the one or more securing tabs 124, the handgrip 116 extends away from the top edge 122 in a direction opposite the bottom edge 126. The handgrip 116 includes a pair of top panels 136,138 each joined to an adjacent side panel 118,120 and extending along the top edge 122 of the body 106. The top panels 136,138 are separated by a recess 140 disposed between the top panels 136,138 and extending away from the top edge 122. The recess 140 terminates at a stop wall 142 including a flat upper surface 141 extending between and offset from the top panels 136 by side walls 144,146. The flat upper surface 141 additionally includes a number of retaining tabs 143 that extend upwardly from the upper surface 141 adjacent the stop wall 142. In the illustrated exemplary embodiment of FIG. 10, the retaining tabs 143 are wedge-shaped with a narrow end 161 adjacent the stop wall 142 and a wide end 163 spaced from the narrow end 161 to provide a locking surface 165 extending outwardly from and generally perpendicular to the upper surface 141.

A bottom surface 145 of the recess 140 includes an engagement cavity 147 therein. In the illustrated exemplary embodiment of FIGS. 7-10, the engagement cavity 147 extends into the bottom surface 140 but not through the encasement 102 and includes a first slot 149 approximately centered in the bottom wall 145 and extending in a direction between the stop wall 142 and the interior 104 of the body 106. The engagement cavity 147 additionally includes a second slot 151 that intersects the first slot 149 opposite the stop wall 142 and extends in a direction between the side walls 144,146 of the recess 140. The second slot 151 is not centered on the first slot 149 but includes a short portion 153 extending from the first slot 149 towards the side wall 146 and a long portion 155 extending opposite the short portion 153. The engagement cavity 147 additionally includes a locking shoulder 157 disposed between the long portion 155 of the second slot 151 and the first slot 149.

The handgrip 116 further includes a grip bar 148 connected to the top panels 136,138 and the stop wall 142 opposite the top edge 122. The grip bar 148 extends from one side edge 118 adjacent the side panel 112 across and spaced from the top edge 122 to the opposed side edge 120 adjacent the associated side panel 114. While the shape of the grip bar 148 can be selected as desired, in the illustrated exemplary embodiment the grip bar 148 includes a first angled section 150 disposed along or aligned with the top wall 136, a flat section 152 aligned with the recess 140, and a second angled section aligned with the top wall 138. The grip bar 148 is held in the spaced location relative to the top walls 136,138 and the recess 140 by a pair of struts 156 extending between opposite sides of the recess 140 and the grip bar 148. Each of the first angled section 150, the flat section 152 and the second angled section 154 are spaced by the struts 156 from the aligned top walls 136, 138 and recess 140, respectively, to define grip apertures 158,160,162 therebetween. While the shape of the grip apertures 158-162 can be selected as desired, in the illustrated exemplary embodiment the shape of the grip apertures 158 and 162 are mirror images of one another, while the grip aperture 160 is aligned with centerline of encasement 102.

In order to assist the technologist in effectively grasping and holding one or more of the grip apertures 158-162, one or more of the grip apertures 158-162 can include one or more grip enhancement structures 164 that form a non-homogeneous cross-section of at least a portion of the grip bar 148 around the grip apertures 158-162. The grip enhancement structures 164 can take a variety of forms and shapes as desired, including various friction-enhancing coatings, strips or panels attached to the grip bar 148 of the handgrip 116 around the grip apertures 158-162 in areas that are directly engaged by the hands of the technologist when manipulating the grid handle 100 via the grip bar 148.

In the illustrated exemplary embodiment, the grip enhancement structures 164 take the form of one or more protrusions 166 formed directly on the grip bar 148 within one or more of the grip apertures 158-162. The protrusion 164 can extend from the grip bar 148 into the grip aperture 158-162 to separate a finger recess 168 from the remainder of the grip aperture 158-162. In use, a technologist can place one or more fingers within the finger recess 168, such that the finger(s) rests against the protrusion 166 to provide a structural barrier or stop to the sliding of the finger along the grip bar 148 and out of the finger recess 168. In this manner, the protrusion 166 and finger recess 168 enable the technologist to more easily retain a proper grip on the grip bar 148 in the desired location during the manipulation of the grid handle 100.

Looking now at FIGS. 4, 7-8 and 11-15, to effectively retain the detector 62 within the interior 104 of the encasement 102, the grid handle 100 includes an auto-locking mechanism 200. The auto-locking mechanism 200 includes a latch 202 slidably retained within the recess 140 and a lock 204 inserted through the latch 202 and moveably engaged with the encasement 102.

Referring now to FIGS. 7 and 11-13, the latch 202 is formed of a suitable x-ray transparent material, for example, a material similar to that forming the encasement 102, and includes a body 206. The body 206 includes a bottom wall 208 including an elongate slot 207 formed therethrough, the slot 207 including an enlarged section 209 offset to one side with regard to the center of the slot 207. The body 206 additionally includes a pair of opposed side walls 210,212 extending upwardly from the bottom wall 208, and a pair of opposed end walls 214,216 extending upwardly from the bottom wall 208 and joining the side walls 210,212 to define an open interior or groove 218 above the bottom wall 208. Opposite the bottom wall 208, the body 206 includes an open upper end 220 with a securing flange 222 extending outwardly from the open upper end 220 over the end wall 214 and a retaining flange 224 extending outwardly from the open upper end 220 over the end wall 216.

The body 206 of the latch 202 has a size and/or shape complementary to the shape of the recess 140 to enable the body 206 to slide within the recess 140 during operation of the latch 202. Further, each side wall 210,212 can include an outwardly projecting spur 226 disposed opposite the open upper end 220. The spurs 226 are slidably retained within complementary shaped channels 228 located in the lower end of opposed sides 145 of the recess 140 to retain and align the body 206 within the recess 140 as the body 206 slidably moves within the recess 140. Also, the retaining flange 224 is disposed in alignment with the flat, upper surface 143 of the top wall 142 to enhance the alignment of the body 206 with the recess 140 during movement of the latch 202 and to engage the retaining tabs 143 on the upper surface to assist in holding the latch 202 within the recess 140.

Figure 17:
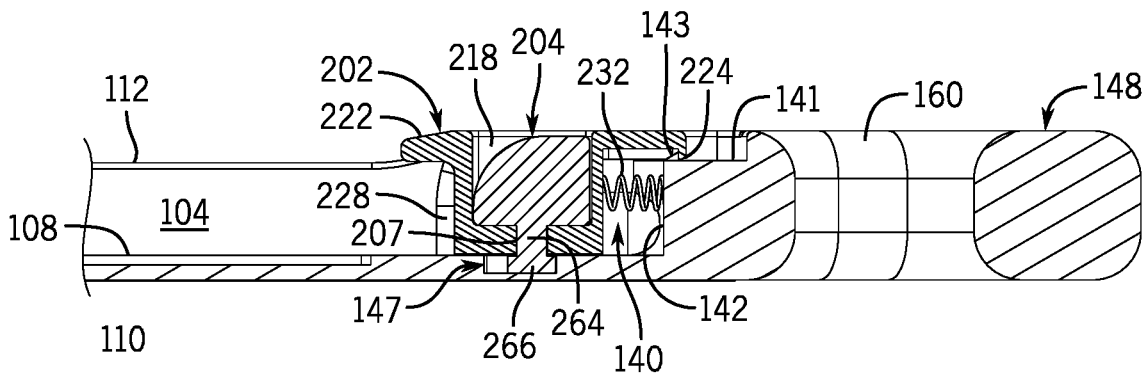
FIG. 17 is a cross-sectional view along line 17-17 of FIG. 16E.
Figure 18:
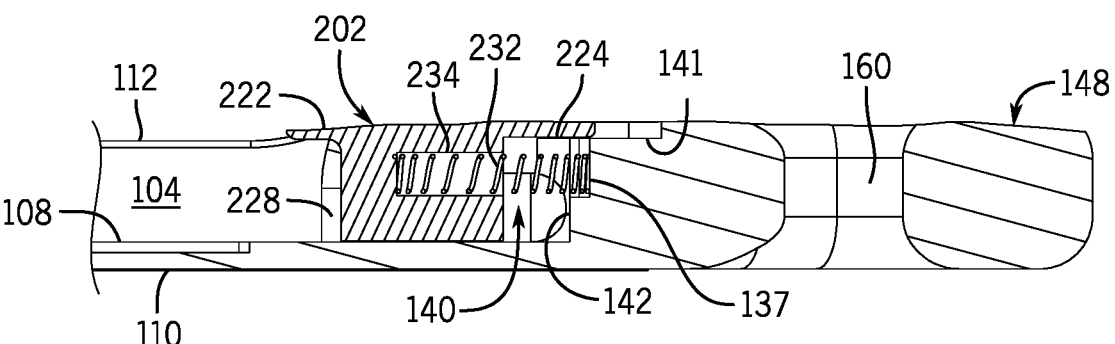
FIG. 18 is a cross-sectional view along line 18-18 of FIG. 16E.

The body 206 of the latch 202 is biased outwardly from the recess 140 towards the interior 104 of the encasement 102 by one or more first biasing members 230 engaged between the body 206 and the stop wall 142 of the recess 140. As best shown in the illustrated exemplary embodiments of FIGS. 7, 17 and 18, the first biasing members 230 take the form of springs 232 partially inserted within bores 234 formed in the end wall 216. The springs 232 extend out of the bores 234 into contact with the stop wall 142, and optionally to seat within notches 137 formed in the stop wall 142. In this configuration, when the latch 202 is slid along the recess 140 away from the interior 104, the springs 232 are compressed between the body 206 and the stop wall 142. This compression causes the springs 232 to continually press the body 206 of the latch 202 away from the stop wall 142 and into the interior 104. The engagement of the aligning flange 222 over the flat upper surface 141 of the stop wall 142 and the engagement of the spurs 226 within the channels 228 maintains the alignment of the body 206 in the recess 140 to enable the spring 232 to bias the movement of the latch 202 in the desired direction towards the interior of the encasement 102.

Referring now to FIGS. 4, 7 and 14-15, the lock 204 is formed of a suitable x-ray transparent material, for example, a material similar to that forming the encasement 102, and having a body 250. The body 250 includes a bottom wall 252 and a rear wall 254 extending outwardly from the bottom wall 252 along one edge of the bottom wall 252. The rear wall 254 includes an engagement member 256 formed thereon and extending outwardly therefrom, which in the illustrated exemplary embodiment of FIGS. 7 and 14-15 include a ridge 258 extending from the rear wall 254 over the bottom wall 252 and defining a pair of engagement surfaces 260,262 on each side of the ridge 258. To grasp the lock 204, an individual can pinch or otherwise engage the engagement surfaces 260,262 on each side of the ridge 258. The lock 204 additionally includes a stem 264 disposed on the bottom wall 252 opposite the ridge 258. The stem 264 extends outwardly from the bottom wall 252 opposite the engagement member 256 and includes a tab 266 on the stem 264 spaced from the bottom wall 252, where the tab 266 has a perimeter larger than the perimeter of the stem 264.

Figures 14, 15, 16A:
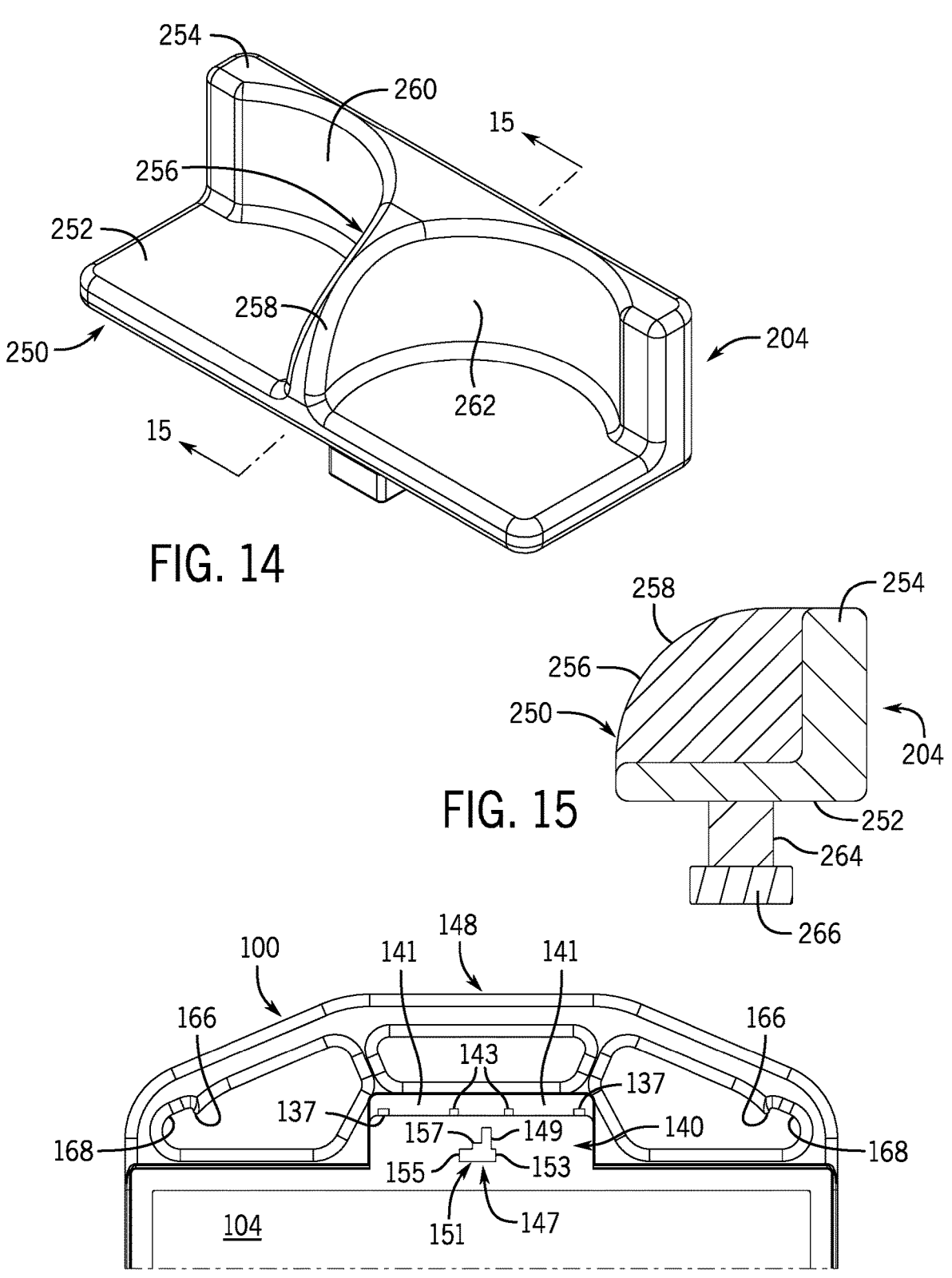
FIG. 14 is an isometric view of a lock disposed on the auto-locking latch on the grid handle of FIG. 4, according to an exemplary embodiment of the disclosure.
FIG. 15 is a cross-sectional view along line 15-15 of FIG. 14.
FIGS. 16A-16E are partially broken away, isometric view of the process for installation of the auto-locking latch on the encasement of the grid handle of FIG. 4, according to an exemplary embodiment of the disclosure.
Figure 16B:
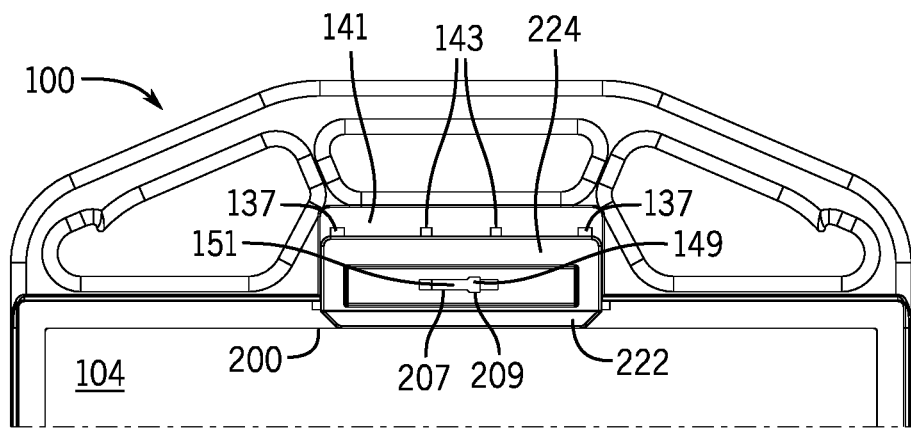

Looking now at FIGS. 7 and 16A-18, to engage the auto-locking mechanism 200 with the encasement 102, as shown in FIGS. 16A-16B, initially the springs 232 are inserted within the bores 234 of the latch 202. The spurs 226 on the latch 202 are aligned with and slid into the channels 228 in the side walls 144,146 of the recess 140, with the springs 232 contacting the stop wall 142. The latch 202 is slid into the recess 140 until the elongate slot 207 is aligned with the second slot 151 of the engagement cavity 147, as best shown in FIG. 16B. In this position, the enlarged section 209 of the elongate slot 207 is positioned in alignment with the first slot 149 and the retaining flange 224 is positioned adjacent the retaining tabs 143. Also, the second biasing members 230/springs 232 are engaged with the stop wall 142, and optionally seated in notches 137 formed in the stop wall 142 that are aligned with the bores 134.

Figure 16C:
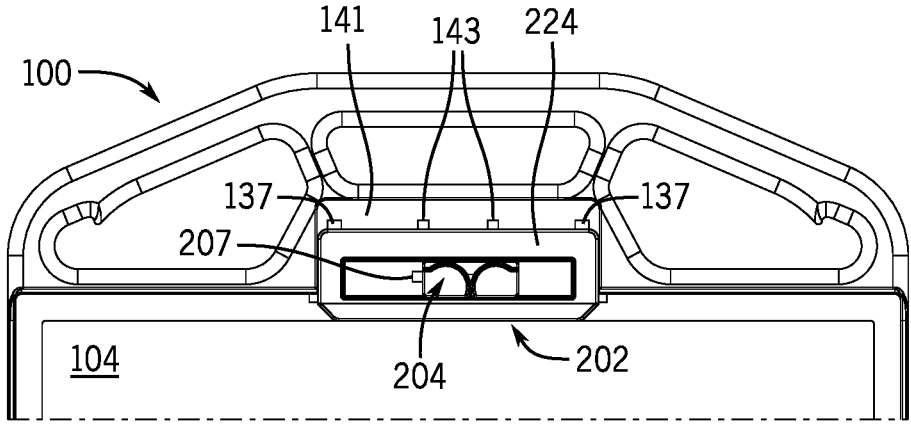
Figure 16D:
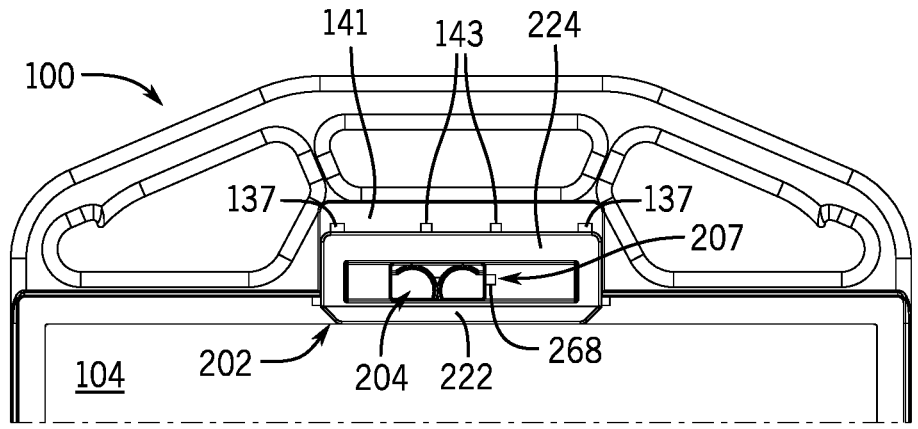
Figure 19:
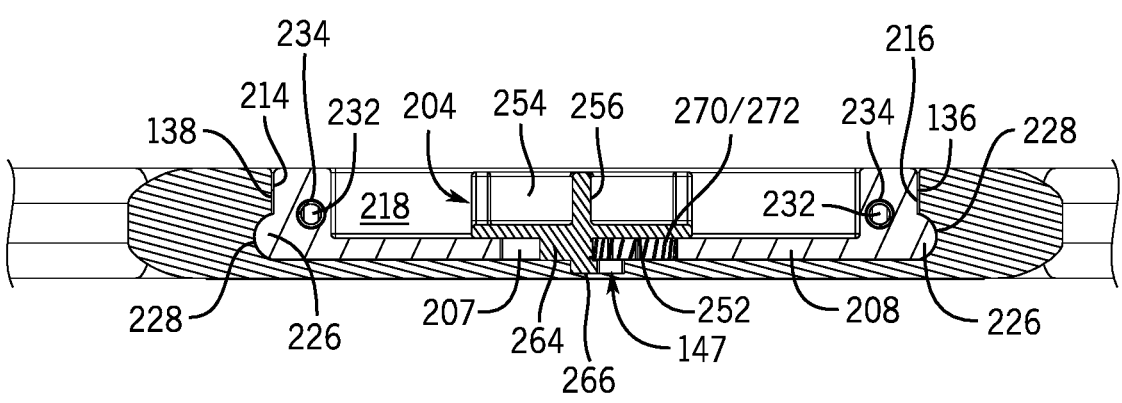
FIG. 19 is a cross-sectional view along line 19-19 of FIG. 16E.
Figure 20:
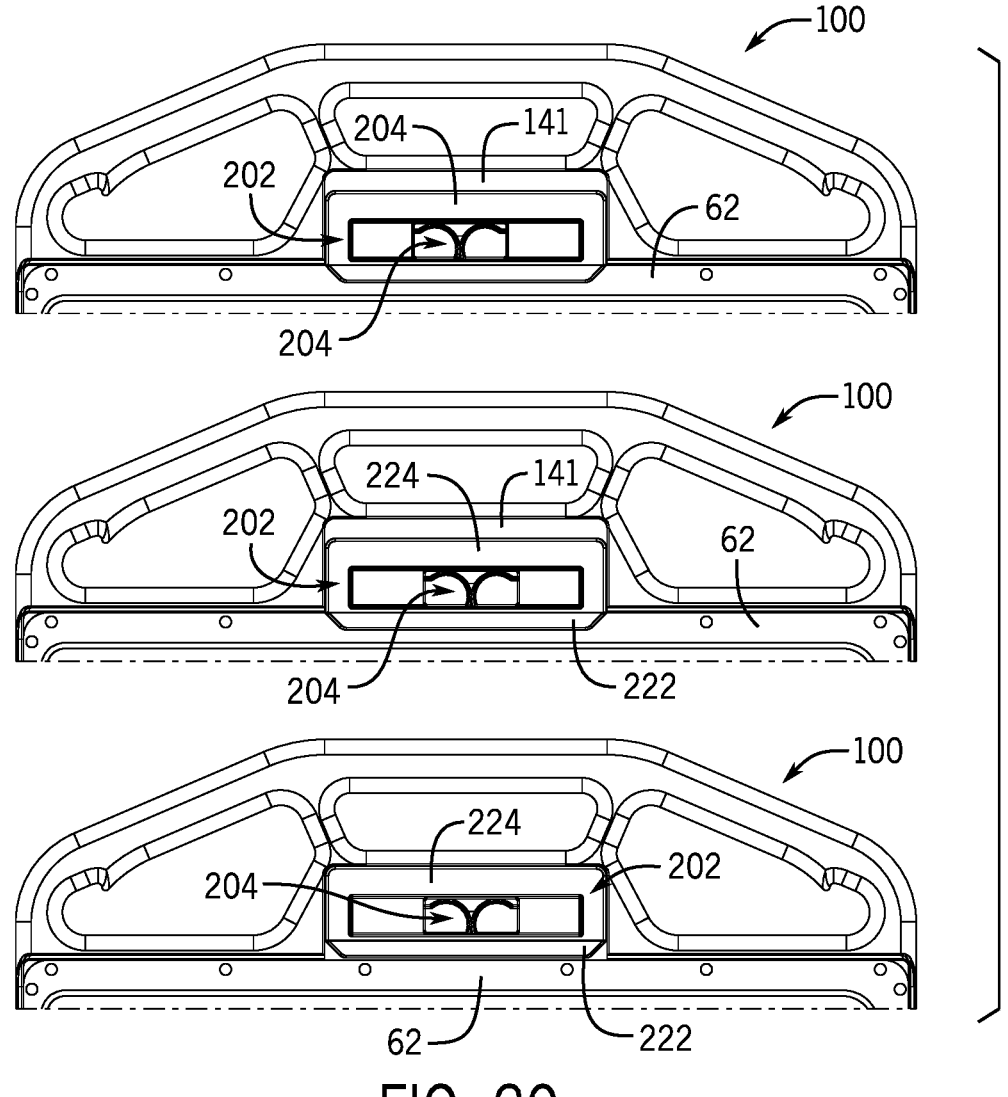
FIG. 20 illustrates partially broken away, isometric views of the operation of the auto-locking latch on the grid handle of FIG. 4.

Referring now to FIG. 16C, with the latch 202 in this position, the tab 236 on the stem 234 disposed on the lock 204 is then inserted through the enlarged section 209 of the elongate slot 207 and into the second slot 151 to position the lock 204 within the groove 218 of the latch 202. As shown in FIGS. 16D and 19, after the tab 236 is inserted into the second slot 151, the lock 204 is moved within the groove 218 to correspondingly move the stem 234 along the elongate slot 207 to position the tab 236 at the end of the second slot 151 nearest the side wall 144. In this position, the lock exposes a gap 268 at the end of the elongate slot 207 adjacent the side wall 146. A second biasing member 270 is then inserted through the gap 268 into the second slot 151 in the body 106 of the encasement 102. The second biasing member 270 can take the form of a coil spring 272 and extends from the short portion 153 of the second slot 151 into engagement with the tab 236. The second biasing member 270 is retained within the elongate slot 207 and engages the stem 264 of the lock 204 to function to bias the tab 236 and the lock 204 into the long portion 155 of the second slot 151 and out of alignment with the first slot 149.

Figure 16E:
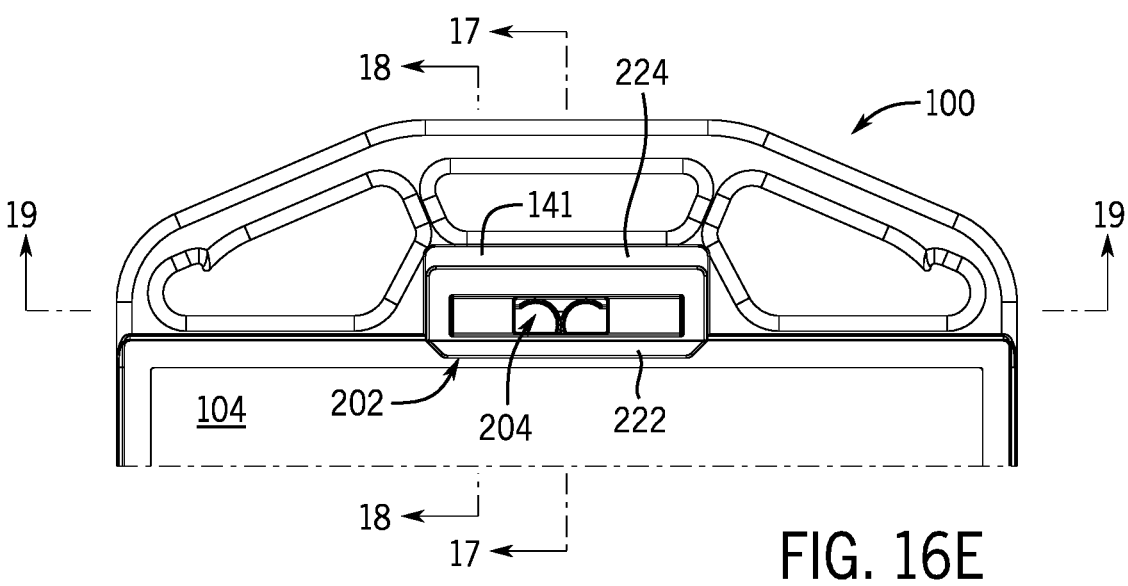

Finally, as shown in FIG. 16E, the lock 204 is moved along the second slot 151 against the bias of the second biasing member 270 to align the tab 236 with the first slot 149. In this position, the latch 202 can be slid further into the recess 140 against the bias of the first biasing members 230, with the tab 236 moving along the first slot 149, to urge the retaining flange 224 over the retaining tabs 133 on the upper surface 132. The retaining flange 224 can continue to slide along the upper surface 132, but the engagement of the retaining flange 224 with the locking surfaces 165 on the retaining tabs 133 functions to limit the motion of the latch 202 as a result of the bias of the first biasing members 230.

In operation of the auto-locking mechanism 200, referring now to FIGS. 17-20, initially in a locked position the latch 202 is biased towards the interior 104 of the encasement 102 to engage the retaining flange 224 with the retaining tabs 133. In this position, the tab 236 of the lock 204 is aligned with and biased into engagement with the locking shoulder 157 by the second biasing member 270. Further, in this position the retaining flange 222 is positioned over the interior 104 of the encasement 102, and over an edge of a detector 62 located within the interior 104.

To unlock the mechanism 200, the lock 204 is grasped and slid along the elongate slot 207 in the latch 202 against the bias of the second biasing member 270 to move the tab 236 away from the locking shoulder 157 and into alignment with the first slot 149. In the unlocked position, the retaining flange 222 is still positioned in the retaining position over the interior 104 of the encasement 102.

To open the mechanism 200, from the unlocked position the latch 202 is moved into the recess 140 against the bias of the first biasing members 230 to move the retaining flange 222 over the recess 140 and out of the interior 104. In this position a detector 62 can freely be inserted within the interior of the encasement 102 by engaging the detector 62 with the securing tabs 1124 and subsequently pivoting the detector 62 into the interior 104 of the body 106, or removed from the interior 104 using the reverse steps.

Further, as result of the bias of the first biasing member 230 the latch 202 is always urged into the closed position when not being actively moved by the user. Further, the lock 204 is continuously urged into the locked position by the second biasing member 270. In this manner, the auto-locking mechanism 200 operates to automatically engage and lock the mechanism 200 over the interior 104 to hold a detector 62 within the interior 104 of the encasement, thereby avoiding inadvertent disengagement of the detector 62 from the encasement 102 of the grid handle 100.

In addition, the construction of the auto-locking mechanism 200 only requires the latch 202, the lock 204 and the biasing members 230,270 for installation and operation of the mechanism 200 on the grid handle 100, without the need for any fasteners or other components for the attachment of the auto-locking mechanism 200 to the grid handle 100.

Also, when inserted within the interior 104 of the encasement 102, due to the positioning of the grid within the body 106, the detector 62 is automatically aligned with the grid when positioned fully within the interior 104. In this manner, there is no need for the adjustment of the detector 62 within the grid handle 100 for effective use of the grid with the detector disposed within the grid handle 100. Also, in situations where it is desired not to employ the grid located within the body 106, the configuration of the encasement 102 enables the detector 62 to be placed within the interior 104 of the body 106 in a reversible manner such that the detector 62 is disposed between the x-ray emitter 52 and the grid located within the grid handle 100.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:
1. A grid handle for a detector utilized with a mobile x-ray device, the grid handle comprising:
a. an encasement for releasably receiving and retaining the detector therein, the encasement comprising:
i. a body including an interior adapted to receive the detector therein;
ii. a handgrip extending along a top edge of the body; and
iii. an auto-locking mechanism disposed on the body and operable to secure the detector within the interior of the body; the auto-locking mechanism comprising:
i. a latch moveably mounted to the body;
ii. a first biasing member engaged between the latch and the body;
iii. a lock moveably mounted to the latch; and
iv. a second biasing member engaged between the lock and the body.
2. The grid handle of claim 1, wherein the latch comprises a pair of spurs disposed on opposed sides of the latch, wherein the spurs are slidably disposed within channels formed in the body.
3. The grid handle of claim 2, wherein the spurs have a semi-circular cross-section.
4. The grid handle of claim 1, wherein the first biasing member urges the latch in a first direction at least partially into the interior of the body, and wherein the second biasing member urges the lock in a second direction generally perpendicular to the first direction.
5. The grid handle of claim 4, wherein the lock comprises:
a. an engagement member extending outwardly from one side of the lock; and
b. a locking stem extending outwardly from an opposite side of the lock.
6. The grid handle of claim 5, wherein the latch includes an elongate slot therein and wherein the stem is inserted through the elongate slot into engagement with the body.

7. The grid handle of claim 6, wherein the latch comprises a groove in which the elongate slot is formed and within which the lock is slidably positioned.

8. The grid handle of claim 7, wherein the body comprises an engagement cavity within which the locking stem is disposed.

9. The grid handle of claim 8, wherein the engagement cavity comprises:

a. a first slot extending parallel to the first direction; and b. a second slot that at least partially intersects the first slot and extends parallel to the second direction.

10. The grid handle of claim 1, further comprising at least one securing tab disposed along a bottom edge of the body opposite the handgrip.

11. The grid handle of claim 10, further comprising a pair of securing tabs disposed on the bottom edge of the body, the pair of securing tabs spaced from one another to define a connector space therebetween.

12. The grid handle of claim 1, wherein the handgrip comprises a grip bar connected to the body at each end and defining at least one grip aperture between the body and the grip bar, wherein the grip bar does not have a homogeneous cross-section.

13. The grid handle of claim 12, further comprising at least one grip enhancement structure disposed on the grip bar.

14. The grid handle of claim 13, wherein the at least one grip enhancement structure on the grip bar is a protrusion extending into the at least one grip aperture.

15. The grid handle of claim 1, wherein the auto-locking mechanism consists of:

a. the latch moveably mounted to the body;

b. the first biasing member engaged between the latch and the body;

c. the lock moveably mounted to the latch and the body; and d. the second biasing member engaged between the lock and the body.

16. A method for positioning a detector within a grid handle, the method comprising the steps of:

a. providing a grid handle comprising:
  i. an encasement for releasably receiving and retaining the detector therein, the encasement comprising:
    1. a body including an interior adapted to receive the detector therein;
    2. a handgrip extending along a top edge of the body; and
    3. an auto-locking mechanism disposed on the body and operable to secure the detector within the interior of the body;
    the auto-locking mechanism comprising:
    i. a latch moveably mounted to the body;
    ii. a first biasing member engaged between the latch and the body;
    iii. a lock moveably mounted to the latch; and
    iv. a second biasing member engaged between the lock and the body;

b. disengaging the lock on the latch;

c. moving the latch from a closed position to an open position;

d. placing the detector within the interior of the body; and e. releasing the latch to move into the closed position over at least a portion of the detector.

17. The method of claim 16, wherein the step of disengaging the lock on the latch comprises moving the lock with respect to the latch against the bias of the second biasing member.

18. The method of claim 16, wherein the step of moving the latch comprises moving the latch with respect to the body against the bias of the first biasing member.

19. The method of claim 16, wherein the step of placing the detector within the interior of the body comprises the steps of:

a. engaging an end of the detector with at least one securing tab disposed on the body opposite the auto-locking mechanism, and b. pivoting the detector into the interior of the body.

20. The method of claim 19, wherein the at least one securing tab exposes a charging connector on the end of the detector, and wherein the method further comprises the step of engaging the charging connector with a charging port disposed within a storage bin on a mobile x-ray device.

* * * * *